United States Patent
Perrett et al.

(10) Patent No.: US 9,541,557 B2
(45) Date of Patent: Jan. 10, 2017

(54) IN-SITU REAGENT FOR DETECTION OF PROTEINS

(75) Inventors: David Perrett, London (GB); Soledad Cecilia Ruiz Antoli, London (GB); Nanda Kishore Babu Nayuni, London (GB)

(73) Assignee: Queen Mary & Westfield College, University of London, London (GB)

( * ) Notice: Subject to any disclaimer, the term of this patent is extended or adjusted under 35 U.S.C. 154(b) by 0 days.

(21) Appl. No.: 13/817,540

(22) PCT Filed: Aug. 19, 2011

(86) PCT No.: PCT/GB2011/001244
§ 371 (c)(1),
(2), (4) Date: Jun. 14, 2013

(87) PCT Pub. No.: WO2012/022945
PCT Pub. Date: Feb. 23, 2012

(65) Prior Publication Data
US 2013/0260470 A1   Oct. 3, 2013

(30) Foreign Application Priority Data
Aug. 20, 2010   (GB) .................................. 1014028.3

(51) Int. Cl.
*G01N 33/68* (2006.01)
*G01N 33/60* (2006.01)

(52) U.S. Cl.
CPC .................................. *G01N 33/6839* (2013.01)

(58) Field of Classification Search
CPC .................................. G01N 33/6839
USPC ............................ 436/86, 518; 435/69.1, 7.1
See application file for complete search history.

(56) References Cited

U.S. PATENT DOCUMENTS

2005/0282229 A1* 12/2005 Su .................... G01N 33/48721
  435/7.1
2005/0287548 A1* 12/2005 Bao .......................... B82Y 5/00
  435/6.11

OTHER PUBLICATIONS

Lochmann, D. et al. "New protamine quantification method in microtiter plates using o-phthaldialdehyde/N-acetyl-L-cysteine reagent". Int J Pharm. 2004. 283(1-2):11-17.
McCormick, P. et al. "A designed experiment for evaluation of the OPA method for cleaning studies of medical devices". Biomed Instrum Technol. 2007. 41(4):324-331.
Smith, A. et al. "Residual protein levels on reprocessed dental instruments." J Hosp Infect. 2005. 61(3):237-241.
Verjat, D. et al. "Flourescence-assay on traces of protein on re-usable medical devices: cleaning efficiency." Int J Pharm. 1999. 179(2)267-271.
Mozersky, S. "Off-line and on-line assay of membrane protein with o-phthaldialdehyde by flow-injection with post-column reaction", Analytica Chimica Acta, 1900, 231:249-257.
Sharov et al., "Diastereoselective reduction of protein-bound methionine sulfoxide by methionine sulfoxide reductase", FEBS Letters, 1999, 455:247-250.

* cited by examiner

*Primary Examiner* — Rebecca M Fritchman
(74) *Attorney, Agent, or Firm* — Pepper Hamilton LLP

(57) ABSTRACT

The present invention relates to a stable protein and/or amino acid detecting composition that can be used as a reagent for in situ detection, such as on surfaces. The invention also relates to a method for detecting protein and/or amino acid on surfaces using the composition and kits comprising the composition.

14 Claims, 11 Drawing Sheets

IN-SITU REAGENT FOR DETECTION OF PROTEINS

Figure 1A:
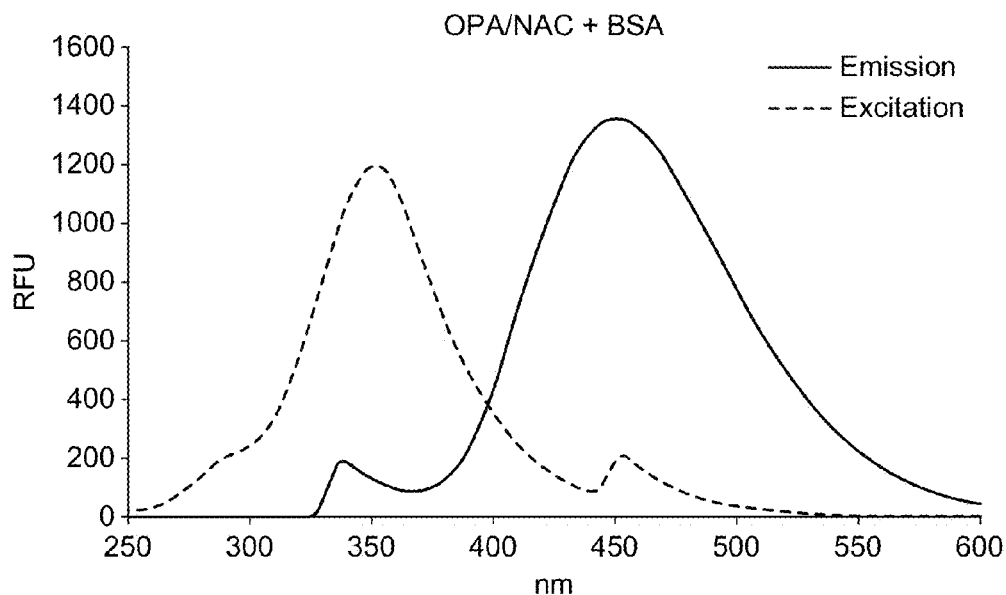

The present invention relates to a stable protein and/or amino acid detecting composition that can be used as a reagent for in situ detection, such as on surfaces. The invention also relates to a method for detecting protein and/or amino acid on surfaces using the composition and kits comprising the composition.

Detecting protein matter such as intact proteins and/or their subunit amino acids and peptides, in particular at trace levels, is an important and standard process in analytical and biological techniques used in a laboratory, clinical and forensic environments. Usually, protein and/or amino acid detection is achieved by using readily available reagents in conjunction with different validated techniques and instrumentation. These methods tend to rely on the reagents reacting with either free amino acids, end terminal amino groups in peptides or end terminal amino groups or side chain, functional groups within the proteins in solution to give visibly coloured or detectable fluorescent products which aid in determining the presence of the analyte in a qualitative and quantitative manner.

Studies have found that the standard sterilisation procedures used in Hospital Sterilisation & Disinfection Units (also known as Sterile Service Departments SSD) are inefficient in decontaminating re-useable surgical instruments (Baxter R. L. et al J Hospital Infection, 2006, 63, 439-44). These studies indicate that residual protein on surgical instruments can be directly related to the potential disease risk including the transfer of vCJD via surgical, particularly neurosurgical, procedures. Therefore, measuring residual protein on surgical instruments in extremely low (nanogram or picogram) quantities is now considered important and should be addressed with urgency.

Ninhydrin (2,2-dihydroxyindene-1,3-Dione) is a chemical used to detect primary and secondary amines. Ninhydrin reacts with the alpha amino group of amino acids. When Ninhydrin reacts with amines, in an optimally heated environment, an intense blue/purple chromophore known as Rubemann's purple (2-[(3-Hydroxy-1-oxoinden-2-yl)imino]-1,3-indandione) is produced. The coloured properties of Ninhydrin allows the visual detection and quantitative analysis of amino acids. Ninhydrin is used in biochemical analysis to determine the amino acid concentration present at the end of various separation techniques, such as chromatography, HPLC or solid phase peptide synthesis.

SSD departments use Ninhydrin in commercially available kits for the qualitative monitoring of the efficiency of the decontamination and/or sterilisation procedure of re-useable surgical and/or dental equipment. The surface of an instrument, which has been autoclaved, heated and washed, is swabbed and the swab is then wetted with the Ninhydrin that is provided in the kit. Once the colour has developed on the swab (upon reacting with an amine), the swab is visually assessed against an arginine standard swab, to determine whether residual protein remains. Ninhydrin is reliant on the presence of freely available amino acids for optimal production of the coloured product. The reagent is most effective in the presence of free amino acids as the amino groups are freely exposed. However, when instruments are washed and autoclaved any free amino acids or amino acids formed from degraded protein is washed away. It has been found that Ninhydrin can detect arginine at a threshold of circa 5 μg/ml compared to Bovine Serum Albumin where the sensitivity is only 500 μg/ml which in practical terms is a very high threshold for detection. The sensitivity is further reduced since the swabbing technique is very inefficient at desorbing proteins from their binding sites. The sensitivity and specificity of Ninhydrin is particularly poor as it is insensitive to residual protein and has a high risk of generating false negatives. Overall Ninhydrin as a reagent and Ninhydrin based kits do not provide the sensitive detection of proteins required for decontamination procedures.

Ortho-phthaldialdehyde (OPA) is another reagent that is used for amino acid detection in chemical and biological research. OPA is used for amino acid detection due to its high sensitivity. The OPA/thiol solution is an alternative reagent to Ninhydrin in amino acid analysis (Stobaugh et al. (1983) Anal Biochem 135, pp.495-504). OPA reacts with primary amines in the presence of a thiol (e.g. mercaptoethanol, ethanethiol or (2R)-2-acetamido-3-sulfanylpropanoic acid commonly known as N-acetyl cysteine (NAC)) to give a highly fluorescent isoindole derivative (Garcia Alvarez-Coque et al. (1989), Anal Biochem 180, pp. 172-176), which can be monitored at Ex/Em=350/450 nm.

Scheme 1: The reaction of OPA with a primary amine in the presence of a thiol to produce a fluorescent 1-akylthio-2-akyl-substituted isoindole.

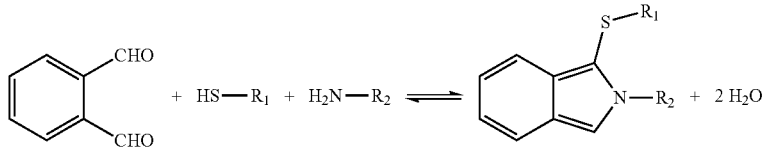

The OPA/thiol reagent has several advantages over other detection methods. It is non-fluorescent and soluble in water. The OPA/thiol reagent reacts with the common amino acids with the exception of cysteine and amino acids to produce detectable fluorescent derivatives. The OPA/thiol reagent reacts rapidly at room temperature to form various detectable fluorophore products (Garcia Alvarex-Coque et al. 1989, supra). The OPA/thiol reagent is convenient, rapid and highly sensitive in detecting free amino acids or proteins in solution and can achieve an accurate quantitative measure of the solubilised proteins. (Verjat et al. (1999), Int J Pharmaceutics 179, pp 267-271).

In contrast to Ninhydrin, the fluorophores formed using the OPA/thiol reagent are different since their structure depends on the amino acid with which the reagent has reacted. However, one of the OPA/thiol's limitations arises from the instability of the isoindole fluorophore derivatives formed. Thus, to achieve analytical precision when using OPA/thiol as a reagent, careful timings are required (Garcia Alvarez-Coque et al 1989, supra). In addition the OPA/thiol reagent has to be made up to 24 hours prior to its use to reduce the background fluorescence and the reagent's stability in a solution is relatively unstable and only lasts for a week at the most.

The above-mentioned methods all have a variety of limitations such as variable protein and/or amino acid specificity, sensitivity and stability of the reagent and/or products formed.

There is thus a need in the art for a reagent that overcomes these limitations.

The present inventors have devised a protein and/or amino acid detecting composition which can be used as an in situ reagent, such as in solution or on surfaces such as on an instrument. for qualitatively and quantitatively determining trace levels of protein matter, and which satisfies the requirements of a reagent to be used in a SSD. The protein and/or amino acid detecting composition is in itself stable and has a prolonged shelf-life and when it reacts with protein matter it produces a stable isoindole fluorophore derivative which can be identified by the use of simple instrumentation and quantified instantly visually or by numerical data means.

In a first aspect of the invention there is provided a protein and/or amino acid detecting composition comprising:
  (a) o-phthaldialdehyde,
  (b) a $C_3$-$C_6$ thiol,
  (c) a buffer with a pH in the range of from about 7.5 to about 10, and
  (d) a surfactant,
wherein the composition further comprises
  (e) a thiol reducing compound.

In one embodiment of the invention, there is provided a protein and/or amino acid detecting composition comprising:
  (a) o-phthaldialdehyde,
  (b) a $C_3$-$C_6$ thiol,
  (c) a buffer with a pH in the range of from about 7.5 to about 10, and
  (d) a surfactant,
wherein the composition further comprises
  (e) a thiol reducing compound at a concentration of about 0.05 mmol/L to about 5 mmol/L.

In other embodiments of the first aspect of the invention, there is provided a protein, and/or amino acid detecting composition comprising:
  (a) about 0.1 mmol/L to about 1.0 mmol/L of o-phthaldialdehyde,
  (b) about 1 mmol/L to about 20 mmol/L of a $C_3$-$C_6$ thiol,
  (c) about 10 mmol/L to about 100 mmol/L of a buffer with a pH in the range of from 7.5 to 10.
  (d) about 0.01 % v/v to about 2% v/v of a surfactant, and
  (e) about 0.05 mmol/L to about 5 mmol/L of the thiol reducing compound.

The concentration and ranges for each of the components are the concentration of each of the components once all the components of the invention have been mixed into the final in-situ protein detecting reagent.

The present invention provides a protein and/or amino acid detecting composition that is stable at room temperature, specific in detecting a wide spectrum of protein matter, sensitive in detecting protein residues at trace levels (such as nanograms or picograms) on surgical and other instrument surfaces and the use of simple instrumentation.

The composition of the invention is therefore suitable for use in detecting protein, and/or amino acid.

A protein is any organic molecule which is composed of covalently linked amino acids. As defined herein, a protein includes peptides and polypeptides. The amino acids can be any of the 20 naturally occurring amino acids or others. Each amino acid is composed of an amine group, a carboxylic acid group and a side chain that varies between different amino acids.

Typically, the protein and/or amino acid detecting composition is an amino group (amine) detecting composition.

The composition of the invention comprises o-phthaldialdehyde. O-Phthaldialdehyde is a compound with the chemical formula of $C_6H_4(CHO)_2$. Phthaldialdehyde is also known as o-phthaldialdehyde, Phthalic aldehyde, phtharal, Phthalic dialdehyde, Disopa, Phthalyldicarboxaldehyde, 1,2-Benzenedicarboxaldehyde, ortho-O-phthaldialdehyde, Orthophthaldialdehyde, Disopa (TN), o-phthaldialdehydes [French], Phthalic dicarboxaldehyde, ortho-Phthalic Aldehyde, Phthaldialdehyde Reagent, o-Phthalic dicarboxaldehyde. It is commonly shortened to OPA (ortho-O-phthaldialdehyde).

OPA is a dialdehyde, consisting of two formyl (CHO) groups attached to adjacent carbon centres on a benzene ring. OPA reacts with amines, in particular primary amines.

In some embodiments, the OPA is immersed in an organic solvent in order to solubilise the OPA and enhance the spray characteristics of the reagent. The organic solvent can be selected from methanol, acetonitrile or other readily volatile solvents. Readily volatile solvents include acetone, ethanol and any solvent which evaporates quickly. Typically, in some embodiments the organic solvent is methanol.

The addition of the organic solvent improves the spray characteristics of the composition and causes the composition to dry quickly so it prevents spreading of the dried protein spots found on surfaces.

In some embodiments, the concentration of OPA can be about 0.1 mmol/L to about 10 mM. In a particular embodiment, the concentration of OPA is about 0.5 mmol/L to about 5 mM. In preferred embodiments, the OPA used in the present invention typically has a concentration of 0.75 mmol/L, 1 mmol/L, 2 mmol/L, 3 mmol/L or 4 mmol/L. Typically in some embodiments the concentration of OPA is 2 mmol/L.

In some embodiments, the organic solvent comprises from about 0.1% v/v to about 10% v/v. In particular embodiments, the organic solvent comprises about 0.5% v/v to about 5% v/v. In preferred embodiments, the organic solvent comprises 0.5% v/v, 0.6% v/v, 0.7% v/v; 0.8% v/v, 0.9% v/v, 1% v/v, 1.5% v/v, 2% v/v, 2.5% v/v, 3% v/v 3.5% v/v, 4% v/v, 4.5% v/v, or 5% v/v.

The composition of the invention also comprises a $C_3$-$C_6$ thiol. The thiol is typically odourless. The thiol should not contain a free amino group, such as cysteine.

A thiol is composed of a sulfur-hydrogen bond (—SH). It is commonly referred to as a thiol group, mercapto group or a sulfhydryl group. In the more traditional sense, thiols are often referred to as mercaptans.

A $C_3$-$C_6$ thiol compound can be any organic compound which contains 3, 4, 5 or 6 carbon atoms and a thiol functional group. The $C_3$-$C_6$ thiol may be saturated or unsaturated and can be unsaturated at one or more positions along the carbon chain. It may be branched, straight chain, cyclic, hydrocarbon radical or it may be hydroxylated at one or more positions along its length. Typically the $C_3$-$C_6$ hydrocarbon chain may be "alkyl" of the general formula $C_nH_{2n+1}$.

Typical alkyl groups include, but are not limited to, methyl, ethyl, propyl, isopropryl butyl, isobutyl, t-butyl, pentyl, isopentyl, hexyl and the like. In the preferred embodiments, the alkyl group is a $C_3$-$C_6$ alkyl.

Specifically, examples of "$C_3$-$C_6$ alkyl groups" include n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like. The alkyl group can be optionally interrupted by one or more oxygen atoms.

In some embodiments, the $C_3$-$C_6$ thiol compound can be selected from N-Acetyl-L-Cysteine (NAC) ((2R)-2-acetamido-3-sulfanylpropanoic acid), 2-Mercaptoethanol (2-Hydroxy-1-ethanethiol), Dithiothreitol (DTT) (2S, 3S)-1,4-Bis-sulfanylbutane-2,3-diol, N-acetyl-D-penicillamine, N-acetyl-cysteamine, N-acetyl-homocysteine and mercaptosuccinic acid. Typically in some embodiments the $C_3$-$C_6$ thiol compound in the protein and/or amino acid detecting composition is N-Acetyl-L-Cysteine.

In some embodiments, the concentration, of the $C_3$-$C_6$ thiol can be about 1 mmol/L to about 20 mmol/L. In particular embodiments, the concentration of the $C_3$-$C_6$ thiol, may be about 5 mmol/L to about 15 mmol/L. In preferred embodiments, the $C_3$-$C_6$ thiol used in the present invention typically has a concentration of 6 mmol/L, 7 mmol/L, 8 mmol/L, 9 mmol/L, 10 mmol/L, 11 mmol/L, 12 mmol/L, 13 mmol/L or 14 mmol/L. Typically in some embodiments the concentration of the $C_3$-$C_6$ thiol is 10 mmol/L.

The composition of the invention also comprises a buffer with a pH in the range of from about 7.5 to about 10.

A buffer is typically a buffet solution that functions to maintain pH at a constant or near-constant value, even when a strong acid or alkali is added. The buffer is typically an aqueous buffer.

A buffet with a pH in the range of from pH 7.5 to pH 10 is an alkaline buffer. The buffer used in the present invention typically has a pH of about pH 8, about pH 9 or about pH 10. In particular embodiments, the buffer has a pH in a range between pH 9 to pH 9.5.

In some embodiments, the $C_3$-$C_6$ thiol compound is in an alkaline buffer solution, with a pH in the range of pH 7.5 to pH 10. Typically, the $C_3$-$C_6$ thiol is in a buffer solution with a pH in the range of about pH 9 to pH 9.5. Typically, the buffer solution is about pH 9.2-9.3.

Examples of buffers which have a pH above pH 7.5 to pH 10 are phosphate buffer and borate buffer. Preferably the buffer is a sodium salt. Preferably, the buffer is not an ammonium salt and is not amino acid based such as glycine buffers.

In particular embodiments, the concentration of the buffer can be about 10 mmol/L to about 100 mmol/L. In particular embodiments, the buffer of the invention may be in a concentration about 25 mmol/L to about 75 mmol/L. In particular embodiments, the buffer of the invention may be in a concentration about 35 mmol/L to about 65 mmol/L. In preferred embodiments, the buffer of the invention has a concentration about 30 mmol/L, 35 mmol/L, 40 mmol/L, 45 mmol/L, 50 mmol/L, 55 mmol/L, 60 mmol/L, 65 mmol/L or 70 mmol/L. Typically in some embodiments the concentration of the buffer is 50 mmol/L.

In preferred embodiments the buffer is Sodium tetraborate ($Na_2B_4O_7$). Typically in some embodiments, the buffer is Sodium tetraborate with pH at pH 9.23 and with a concentration of 50 mmol/L.

The composition of the invention also comprises a surfactant.

A surfactant can be ionic or non-ionic. Examples of ionic surfactants are lecithin (phosphatidyl choline), bile salts and detergents. Examples of non-ionic surfactants include monoglycerides, cremophore, polyethylene glycol fatty alcohol ether, a sorbitan fatty acid ester, a polyoxyethylene sorbitan fatty acid ester, Solutol® HS15, a poloxamer or a combination thereof. Examples of monoglycerides are glyceryl monocaprylate (also termed glyceryl monooctanoate), glyceryl monodecanoate, glyceryl monolaurate, glyceryl monomyristate, glyceryl monostearate, glyceryl monopalmitate, and glyceryl monooleate. Examples of sorbitan fatty acid esters include sorbitan monolaurate, sorbitan monooleate, and sorbitan monopalmitate (Span® 40), or a combination thereof. Examples of polyoxyethylene sorbitan fatty acid esters include polyoxyethylene sorbitan monooleate (Tween® 80), polyoxyethylene sorbitan monostearate, polyoxyethylene sorbitan monopalmitate or a combination thereof.

In some embodiments, the surfactant is non-ionic. In some embodiments the non-ionic surfactant includes but is not limited to Alkyl poly(ethylene oxide), for example polysorbates based on Polyoxyethylene Glycol, such as the Tween® series (Tween® 20, Tween® 80 etc), Brij® series, such as Brij® 35 and the Triton® detergent series (Triton® X-100, etc), Alkylphenol poly(ethylene oxide) or copolymers of poly(ethylene oxide) and poly(propylene oxide) (commercially called Poloxamers® or Poloxamines®). Typically, in some embodiments the surfactant and/or detergent is Triton® X-100.

The surfactant denatures the protein residues especially hydrophobic protein residues so that they react more readily with the detecting composition.

Triton® X-100 has the chemical formula ($C_{34}H_{22}O(C_2H_4O)_n$) and is commonly used in laboratories as a detergent.

In one or more embodiments, the surfactant comprises from about 0.01% v/v to about 2% v/v. In particular embodiments, the surfactant comprises about 0.05% v/v to about 0.5% v/v. For example, 0.5 ml in 100 ml will amount to 0.5% v/v of 100 ml of the composition. In preferred embodiments, the surfactant comprises 0.06% v/v, 0.07% v/v, 0.08% v/v, 0.09% v/v, 0.1% v/v, 0.2% v/v, 0.3% v/v or 0.4% v/v. Typically the surfactant is at 0.1% v/v.

The composition of the invention also comprises a thiol reducing compound.

Thiol reducing compounds include compounds that contain thiol groups such as dithiothreitol (DTT) and 2-mercaptoethylamine, and those that are phosphines and their derivatives, such as Tris (carboxyethyl) phosphine (TCEP).

In solution, sulfhydryl groups are susceptible to both oxidation and disulfide formation. The presence of a thiol reducing compound in the protein and/amino acid composition aids in preventing the formation of excess disulfides and oxidation between the thiols which are the cause of the instability of the reagent's shelf life and the instability of the products formed in the reaction. It can be inferred that the addition of the thiol reducing compound is the component that stabilises the protein and/or amino acid detecting composition of this invention. The thiol reducing compound is advantageous in that it also enhances the sensitivity of proteins in the final detecting reagent.

In particular embodiments, the concentration of the thiol reducing compound can be about 0.05 mmol/L to about 5 mmol/L. In particular embodiments, the concentration of the thiol reducing compound can be about 0.1 mmol/L to about 2.5 mmol/L. In some embodiments, the thiol reducing compound used in this invention has a concentration about 0.075 mmol/L, 0.15 mmol/L, 0.2 mmol/L, 0.35 mmol/L, 0.4 mmol/L, 0.55 mmol/L, 0.65 mmol/L, 0.75 mmol/L, 0.8 mmol/L, 0.95 mmol/L, 1 mmol/L 2 mmol/L, 3 mmol/L or 4 mmol/L. Typically in some embodiments the concentration of the thiol reducing compound is 0.5 mmol/L.

In particular embodiments, the composition of the invention may further comprise a chelating agent.

Chelating agents are organic compounds capable of forming coordinate bonds with metal ions through two or more atoms of the organic compound. The compound formed by a chelating agent and a metal ion is called a chelate. A chelating agent that has two coordinating atoms is called bidentate; one that has three, tridentate; and so on. The chelating agent can therefore be bidenate, tridentate, tetradentate, pentadentate, hexadentate, septadentate, octadentate, nonadentate or decadentate.

Chelating agents offer a wide range of sequestrants to control metal ions in aqueous mediums. By forming stable water soluble complexes with multivalent metal ions, chelating agents prevent undesired interaction by blocking normal reactivity of metal ions.

In some embodiments, the chelating agents of this invention can include but are not limited to 2,2',2'', 2'''-(ethane-1,2-diyldinitrilo)tetraacetic acid (ethylenediaminetetraacetic acid), Ethylenedinitrilotetraacetic acid, EDTA), EGTA, Diethylene Triamine Penta Acetic Acid (DTPA) or Nitrilo-TriAcetic Acid (NTA). Preferably the chelating agent does not contain an amine.

EDTA with the chemical formula of $C_{30}H_{16}O_8N$ is a good example of a common chelating agent which has nitrogen atoms and short chain carboxylic groups. EDTA is also known as Edetic acid, EDTA free-base, EDTA free-acid, $H_4EDTA$, Diaminoethane-tetraacetic acid, Edetic acid, Edetate, Ethylenedinitrilo-tetraacetic acid, Versene® or ethylenediamine-tetraacetate DTPA with the chemical formula $C_{34}H_{23}N_3O_{10}$ is also know as Diethylenetriamine-N,N,N', N', N''-pentaacetic acid, $H_5$dtpa, Pentetic acid, N,N-Bis(2-(bis-(carboxymethyl)amino)ethyl)-glycine, Diethylenetriamine pentaacetic acid or [[(Carboxymethyl)imino]bis(ethylenenitrilo)]-tetra-acetic acid.

NTA with the chemical formula $C_9H_9NO_6$ is also known as 2,2',2''-nitrilotriacetic acid Triglycollamic acid, Trilone® A, alpha, alpha', alpha''-trimethylaminetricarboxylic acid, Tri(carboxymethyl) amine, Aminotriacetic acid, Hampshire NTA acid, nitrilo-2,2',2''-triacetic acid, Titriplex® or Nitrilotriacetic acid.

In particular embodiments, the concentration of the chelating agent can be about 0.05 mmol/L to about 5 mmol/L. In particular embodiments, the concentration of the chelating agent can be about 0.1 mmol/L to about 2.5 mmol/L. In some embodiments, the chelating agent used in this invention has a concentration about 0.075 mmol/L, 0.15 mmol/L, 0.2 mmol/L, 0.35 mmol/L, 0.4 mmol/L, 0.55 mmol/L, 0.65 mmol/L, 0.75 mmol/L, 0.8 mmol/L 0.95 mmol/L, 1 mmol/L 2 mmol/L, 3 mmol/L or 4 mmol/L. Typically in some embodiments the concentration of the chelating agent is 0.5 mmol/L.

In some embodiments, the concentration of the $C_3$-$C_6$ thiol is five times the concentration of the o-phthaldialdehyde in the composition.

In some embodiments, the concentration of the chelating agent can be equal to the concentration of the thiol reducing compound up to 2 mmol/L.

In some embodiments, the concentration of the thiol reducing compound can be twenty times the concentration of $C_3$-$C_6$ thiol in the composition. Under these conditions the sensitivity of the reagent is enhanced. It must be noted that a high concentration of the thiol reducing compound can reduce the sensitivity of the detecting composition.

The composition is stable at 4° C. for up to 6 months and up to 3 months at room temperature. To reduce the background fluorescence from atmospheric ammonia, the composition can be kept at 4° C. for 24 hours prior to its use. The composition can achieve a low background fluorescence of around 35±10 arbitrary units (RFU) 24 hours after preparation when fresh deionised water is employed.

In the second aspect of the invention, there is provided a process for preparing the protein and/or amino acid composition described in the first aspect of the invention.

A process for making the composition simply requires mixing the components (a), (b), (d) and (e) into the buffer solution (c). The components can be mixed sequentially or simultaneously.

In a third aspect of the invention, there is provided a method for detecting protein and/or amino acid, comprising:
a) applying the composition of the invention to a surface and/or substrate, and
b) detecting fluorescence.

The composition described in the first aspect of the invention can be applied in the form of a spray, swab, solution or any other means known by a person skilled in the art to be suitable.

A spray comprising the composition of the invention can further comprise a bottle or container and an atomiser or spray nozzle or any other suitable means.

The bottle or container of the spray can be any bottle or container. For example, such bottles or containers can be made from glass, plastic or other inert material. The container is not made out of a metal since the metal would oxidise the thiols. Preferably, the container can be clear or opaque.

The atomiser or spray nozzle of the spray of this embodiment of this invention permits the conversion of bulk liquid into a mist (collection of droplets) by passing the liquid through a nozzle allowing an even application of the composition of the invention.

The density of the mist is important as it is directly proportional to the time the detecting composition takes to dry and therefore fluoresce.

The term "swab" comprises any absorbent material, such as rayon or any other absorbent materials known to a person skilled in the art, attached to the end of a stick or wire and used for cleansing or applying. An amount of pressure and/or friction is applied to a surface and/or substrate. The protein and/or amino acid is collected on the swab and the swab is then dipped in the composition of the invention. Alternatively, the swab can be dipped in the composition of the invention and then swabbed, rubbed or pressure and/or friction applied onto a surface and/or substrate.

Typically, the composition of the invention can be applied directly on a surface and/or substrate. The detection of the reaction of the composition of this invention in the presence of a protein and/or amino acid on a surface and/or substrate can be indirectly be measured directly or indirectly. The detection of the reaction of the composition can be stable in the dry form for a year or longer.

A surface and/or substrate on which the composition of the invention is applied can be any surface but not limited to, for example glass, metal (for example stainless steel, titanium, platinum or aluminium), plastic or other inert material or aqueous mediums. In particular, a surface and/or substrate can be surfaces and/or substrates on which protein and/or amino acids may be present, such as but not limited to surfaces of medical or dental devices, laboratory equipment or solutions.

Medical devices include reusable devices that are applied onto or inserted into a patient after decontamination and or sterilisation procedures. Such devices include a catheter, a canula, a scalpel, a needle, a speculum, a stent or forceps. Such devices can further include devices used in dental practices, such as extractors, matrix bands, hand pieces.

In the presence of protein and/or amino acid, the composition of the invention reacts with the protein and/or amino acid to produce an improved and stable fluorophore product. The stable fluorophore emits fluorescence which is then detected. The protein fluorophores on surfaces can be stable in the dry form for a year or longer. Therefore, careful timing of detection to achieve reliable and consistent results is not required when using the detecting composition of this invention.

Detecting fluorescence involves using a beam of light, usually ultraviolet light that excites the electrons in molecules of certain compounds and causes them to emit light of a lower energy, typically, but not necessarily, visible light. The light emitted from the reaction can range from about 300 to about 500 nanometers.

Detection of fluorescence can be carried out using any device which detects fluorescence. Devices that measure fluorescence are called fluorometers or fluorimeters. Two general types of instruments that exist are filter fluorometers, which use filters to isolate the incident light and fluorescent light, and spectrofluorometers, which use diffraction grating monochromators to isolate the incident light and fluorescent light. Various light sources may be used as excitation sources, including but not limited to lasers, photodiodes, and lamps; xenon arcs and mercury-vapor lamps in particular.

Fluorimeters are used to detect fluorescence. A fluorimeter works by producing a light of selected wavelength which excites molecules in the solution and/or substrate of a reaction that has taken place. The light promotes molecules to an excited state in which the light is then emitted and fluorescence is produced. The light is then detected at a given wavelength specific to the reaction taken place.

Yet another suitable device that can measure and detect fluorescence is described in the co-pending PCT patent application claiming priority from application no. GB 1014016.8 entitled "Imaging System and Associate Method for Detection of Protein Contamination" flied on 20 Aug. 2010.

The imaging system and associated method for detecting protein contamination, is capable of providing an image of a surface and/or substrate highlighting the areas where protein residue remains. The system comprises a light tight chamber for receiving the instrument. Inside the chamber are two visible light sources and excitation light sources, for respectively illuminating the chamber with visible and excitation type light. A digital camera is able to capture a first image of the instrument as illuminated by the visible light, and a second image, of patterns of fluorescence produced by the fluorophors emitted from the surface and/or substrate, wherein the surface and/substrate has had the composition of this invention applied. The first and second images are combined to produce a composite image of the instrument highlighting the areas of protein contamination.

For maximum sensitivity, fluorescence requires a combination of light sources with appropriate spectral characteristics (wavelength and intensity) that map the fluorescent characteristics of any protein-fluorophore adjunct and a totally dark environment. Whilst laser beams give very high intensities they have very specific wavelengths that may not map the fluorophore as well as being expensive. Intense lamps such as mercury, xenon and mercury-doped xenon are more suitable of routine protein assays. In addition, the reagent should not in itself fluoresce so lowering the background and increasing the sensitivity is important.

The fluorophore product formed when reacting unstable OPA/NAC reagent with a protein (BSA) fluoresces and the fluorescence is measured using a spectrofluorimeter (FIG. 1a) showing excitation and emission peaks of circa 350 and 450 nanometers, respectively. The fluorophore product formed when reacting stable OPA/NAC reagent with a protein (BSA) (FIG. 1b) also shows excitation and emission peaks of circa 350 and 450 nanometers, respectively. Since the excitation and emission wavelengths are specific to fluorescence derivatisation reactions, it can be inferred that the fluorophore formed when using the stable OPA/NAC reagent is therefore the same.

The great advantage of the composition of this invention as a protein detector is its fluorimetric sensitivity reaching a limit of detection down to nanograms of proteins without the requirement of heating and by requiring an excitation wavelength that is readily achieved with a mercury lamp. The detecting composition is even capable of detecting cytochrome-C traces which is known to be difficult to detect.

The detection of fluorescence can then be measured in a qualitative or quantitative manner.

The qualitative detection of fluorescence can be achieved by any means and/or apparatus which detects light. The fluorescence can be seen visually in a darkened room, or through a suitable filter. The fluorescence can be detected and its intensity measured using a suitable detector and emission filter. This can be a photodiode or for the visualisation as well the fluorescence on a whole instrument can be measured via a digital camera or similar device equipped with suitable filter(s) before a CCD detector mounted in a suitable dark environment and appropriate software. The means and/or apparatus which detects light can be visual or with specialised photographic means comprising filters which allow the fluorescence to be detected.

It can also be achieved by simple instrumentation of using a fluorescent lamp, a mercury lamp or a derivative of a mercury lamp to obtain the appropriate excitation wavelength and then observing the fluorescence through appropriate coloured filters.

The quantitative detection of fluorescence can be determined by producing a series of standards of a known protein composition. A protein which is used as a standard is Bovine Serum Albumin (BSA). An assay of BSA with varying concentrations is produced and the fluorescence emitted in reacting with the composition of the invention is then measured and detected by a fluorimeter or any other suitable device which can detect and quantify the fluorescence produced, so as to produce a standard curve and control.

For detection on surfaces, a series of standards solutions of BSA dried on to a stainless steel strip can be prepared. The standard curves can then be used to measure the relative fluorescence emitted from the reaction of the composition of the invention with a surface and/or a substrate to quantitatively assess the amount of trace protein present on the surface and/or substrate.

In addition to the above detection methods, another suitable imaging system is described in the co-pending application titled "IMAGING SYSTEM AND ASSOCIATED METHOD FOR DETECTION OF PROTEIN CONTAMINATION" filed on 20 Aug. 2010, which relates to a device for capturing an image of the fluorescence emitted from the surface and/or substrate when the composition of this invention is applied onto a surface and/or substrate and allowed to fluoresce.

The imaging system is able to provide a quick, accurate determination of whether a surface and/or substrate is contaminated with protein and the content of the protein residue present, wherein a processor and associated analytical software is further applied.

The visible image of the surface and/or substrate, is advantageous as it can be observed with the naked eye as a quick way of determining whether a surface (for example a surgical scalpel or dental rod) still contains any residual protein after the routine cycle of decontamination before disinfecting and sterilising the re-usable equipment at an SSD. Thereafter, associated software can be used to analyse the images so as to determine the quantitative level of protein contamination.

The composition of the invention can also be used to monitor the removal of proteins from surfaces to confirm that the fluorophore products are readily removed from surfaces and so minimising toxicological problems.

In a fourth aspect of the invention, there is provided a kit for detecting protein and/or amino acid on surfaces comprising a composition of the invention and instructions for use. Typically, the instructions direct the user to use the kit in accordance with the third aspect of the invention.

In a fifth aspect of the invention, there is provided a kit for detecting protein and/or amino acid comprising a composition of the invention and means for applying the composition to a surface and/or substrate and instructions for use. Typically, the instructions direct the user to use the kit in accordance with the second aspect of the invention.

The composition of the invention can be an in situ reagent that can be sprayed onto a surface and/or substrate. In one embodiment of the invention the composition typically comprises about 2 mmol/L of OPA solubilised in methanol. A buffer is made to a pH circa 9 with a concentration of about 50 mmol/L and about 0.1% v/v of a non-ionic surfactant is added and stirred until dissolved. Then about 10 mmol/L of a thiol, typically NAC is added and about 0.5 mmol/L of DTT and stirred. The composition is stored at about 4° C. for approximately 24 hours prior to its use. The composition is then applied onto a surface and/or substrate directly or indirectly. In the presence of protein and/or amino acid the composition reacts with residual protein and/or amino acid on the surface and/or substrate on which it is applied. The reaction produces a stable fluorophore product which emits fluorescence that can be detected in a qualitative and/or quantitative manner by simple instrumentation, such as the use of a fluorescent light e.g. a mercury lamp or a fluorimeter. The fluorescence emitted is then measured against a standard protein curve and the amount of protein and/or amino acid present on the surface and/or substrate is quantified. The amount of protein that is found and quantified can be critical in monitoring the presence of protein in clinical, biological and chemical environments.

The detecting composition of this invention has the following advantages:
  The composition and method is capable of revealing protein residues—on "whole" instruments
  Simple—suitable for use in a SSD environment
  It gives a permanent record
  It is capable of generating quantitative data
  It can be protein specific
  It is at least 100-fold more sensitive than present methodologies towards protein residues
  It generates instantaneous results
  Fast—capable of high throughput and automation
  Instrumentation is readily available and should not use lasers
  It is stable
  The detected products are stable
  The method works on most material surfaces
  It is relatively non-toxic i.e. safe reagent;
  The products can be easily removed from stainless steel surfaces
  Low cost—both capital and running.

The composition of the invention and methods described herein can be used in all aspects of scientific analysis to determine the detection of protein and/or amino acid and/or removal of protein and/or amino acid.

Preferred features for the second and subsequent aspects of the invention are as for the first aspect mutatis mutandis.

Figure 1B:
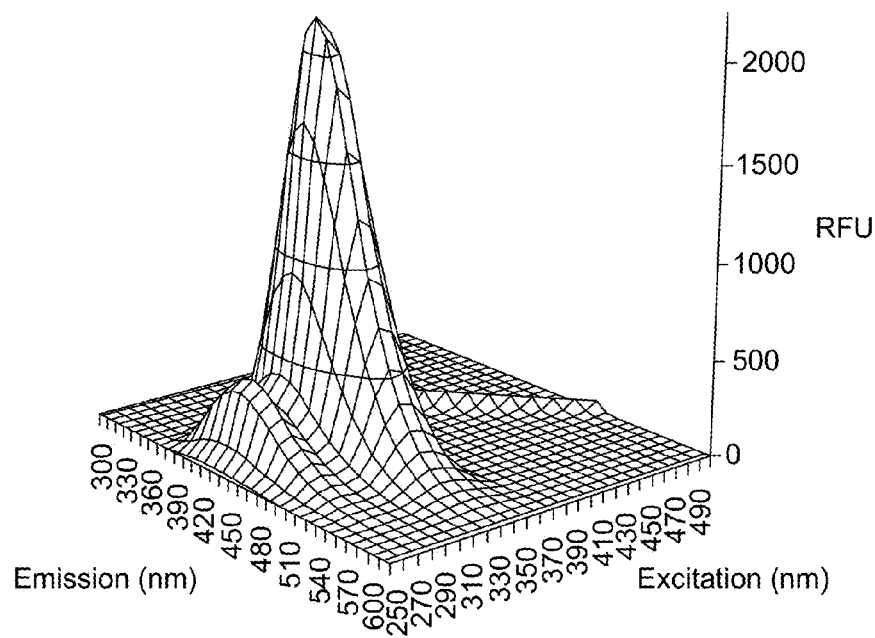

The invention will now be further described by way of reference to the following Examples and Figures which are provided for the purposes of illustration only and are not to be construed as being limiting on the invention. Reference is made to a number of Figures in which:

FIG. 1: shows the excitation and emission spectra of flourophores formed when reacting OPA/NAC reagents with BSA. FIG. 1a shows the excitation and emission peaks of the fluorophores when reacting unstable OPA/NAC reagent with BSA. FIG. 1b shows a 3D scan of the excitation and emission peaks of the fluorophores formed when reacting stable OPA/NAC reagent with BSA.

Figure 2:
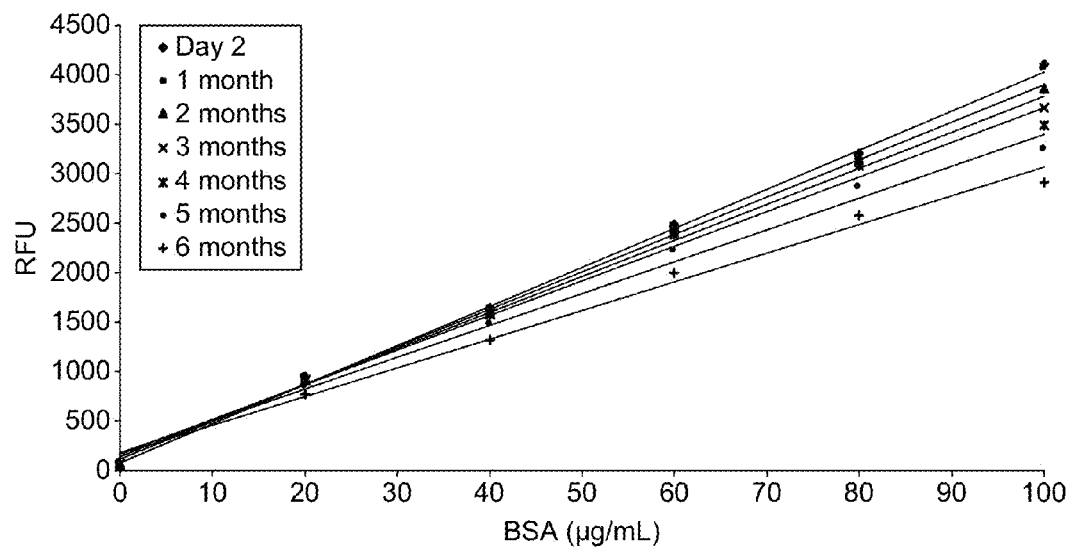

FIG. 2: shows the stabilised OPA/NAC reagent's stability and sensitivity over a period of 6 months when reacted with BSA.

Figure 3:
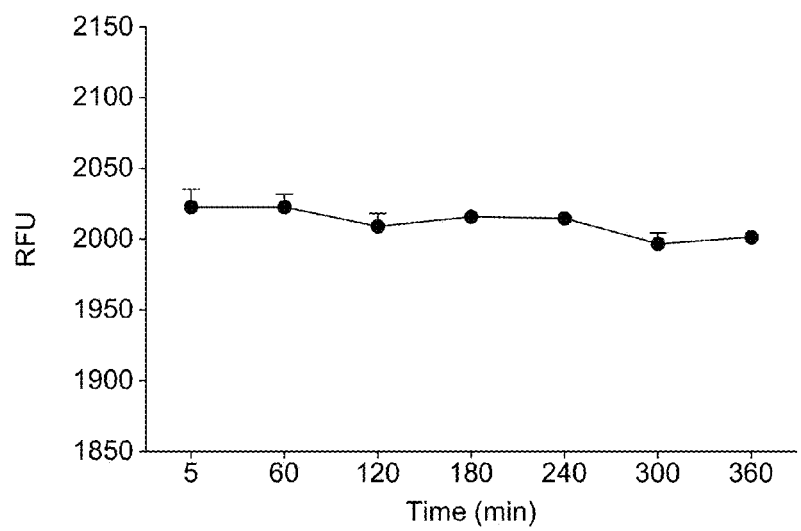

FIG. 3: shows the stability of the fluorophore products formed when using the stabilised OPA/NAC reagent.

Figure 4:
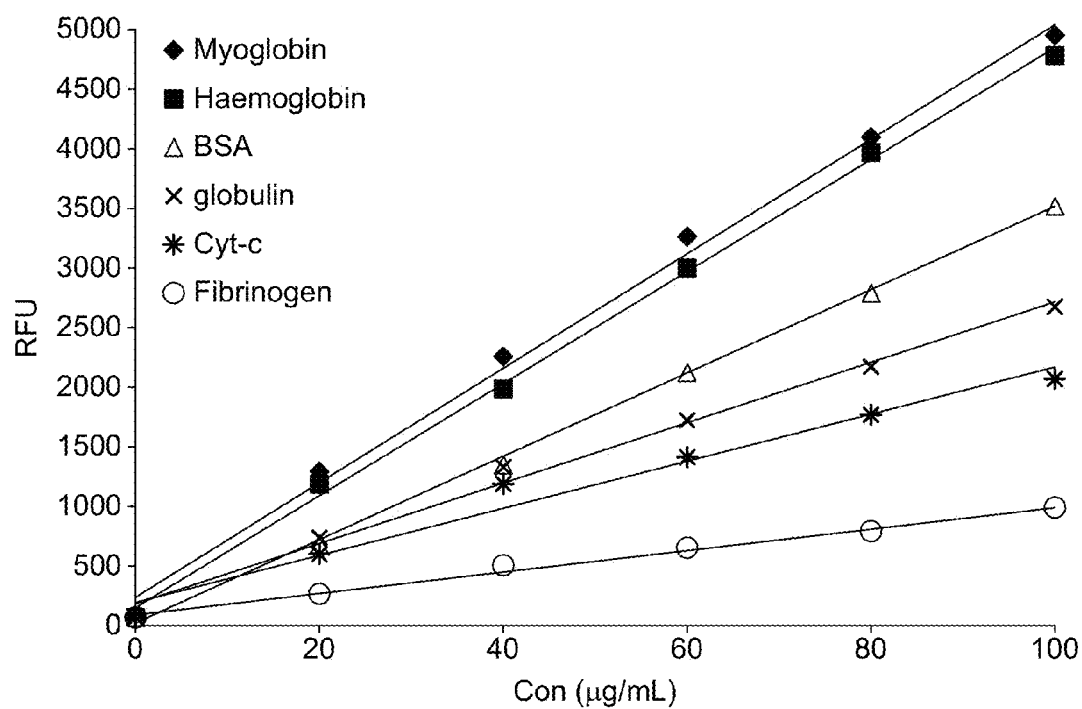

FIG. 4: shows the sensitivity of the stabilised OPA/NAC reagent with proteins in aqueous solution.

Figure 5A:
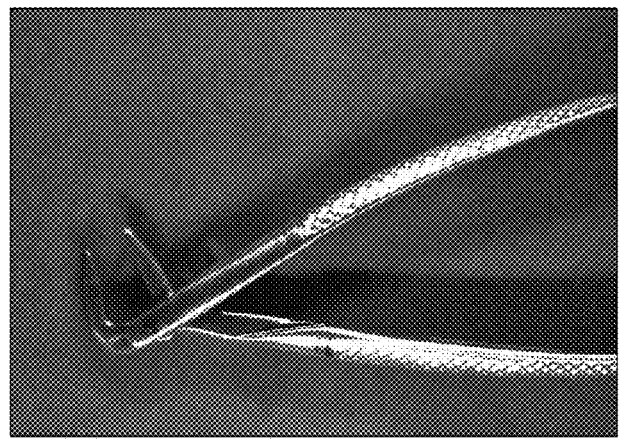
Figure 5B:
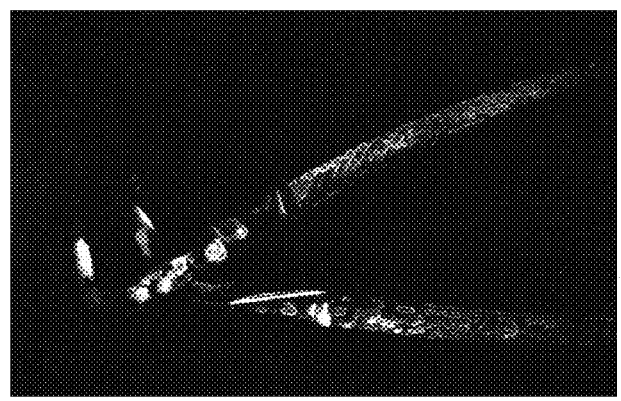
Figure 5C:
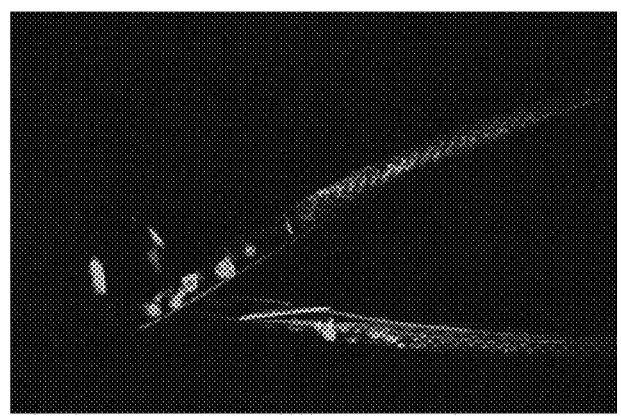

FIG. 5: shows the qualitative analysis obtained using the composition of the invention on a set of stainless steel forceps and screen shots taken with a G-BOX. FIG. 5 (a) shows the screen shot of the white light image of the forceps after SSD cleaning and before the composition of the invention is applied on the forceps; FIG. 5 (b) shows the screen shot of the fluorescence emitted after the composition of the invention has been sprayed onto the forceps; and FIG. 5 (c) shows the screen shot of the false colour overlay showing the protein present.

Figure 6:
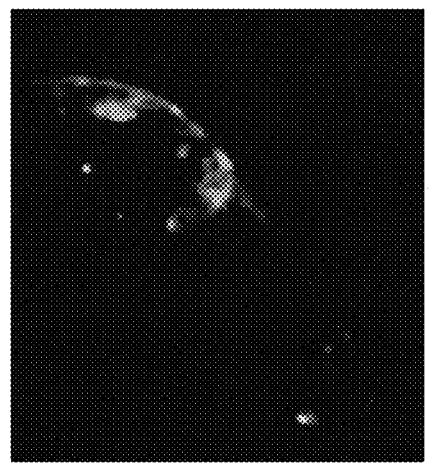

FIG. 6: shows a contaminated surgical scalpel blade sprayed with a 4 month old reagent. Image captured and optically enlarged with a G-BOX.

Figure 7:
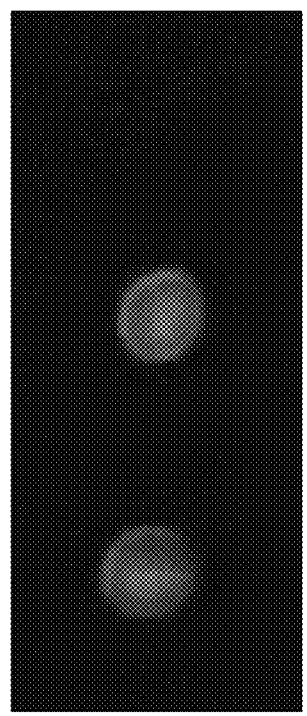
Figure 7:
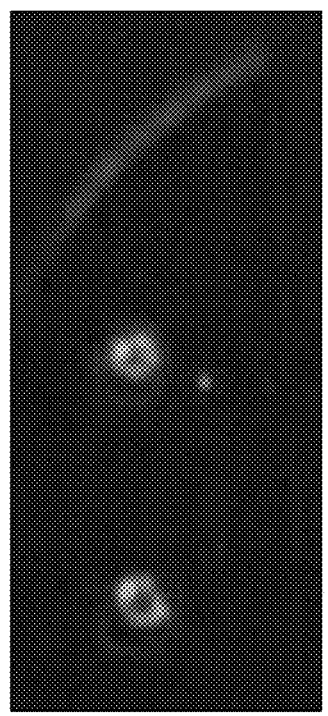

FIG. 7: shows the stability of the fluorophores formed when the stabilised OPA/NAC reagent of this invention reacts with protein. The blade was left on a bench top in open air for 1 month. Image was captured with a G-BOX without re-spraying the instrument with the reagent.

Figure 8A:
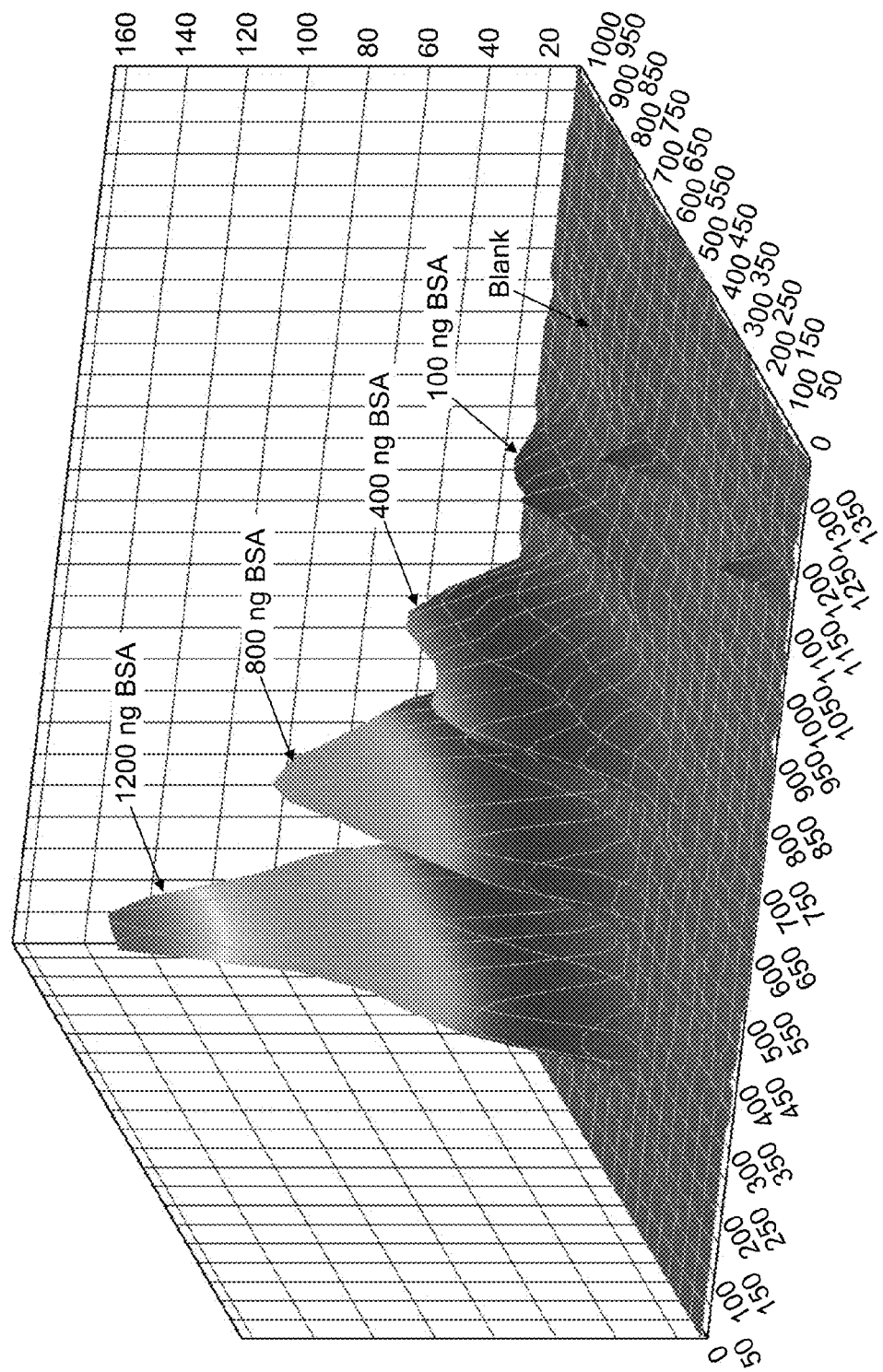
Figure 8B:
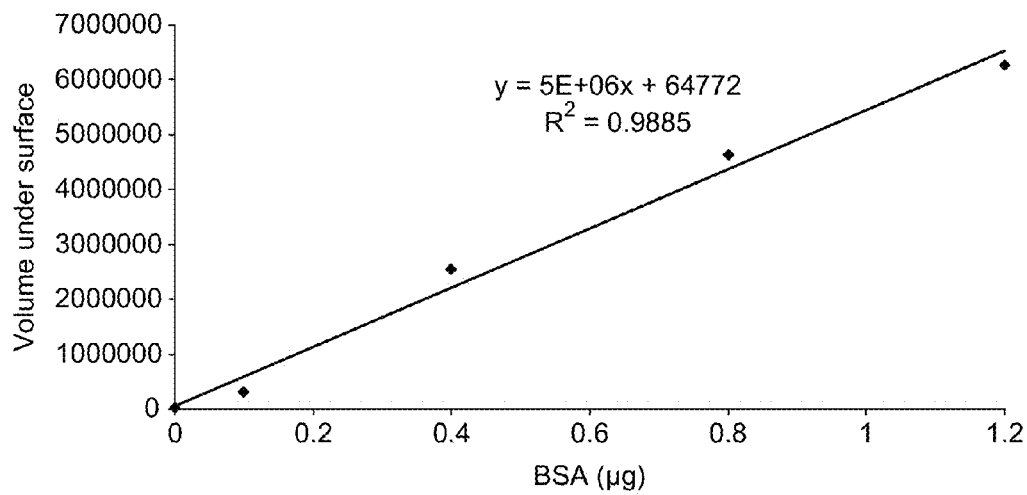

FIG. 8: shows the visualisation of protein matter and semi-quantitative analysis of (the stabilised OPA/NAC reagent) sprayed onto a BSA standard. Image is captured using a G-BOX and analysed using D-Plot software.

Figure 9A:
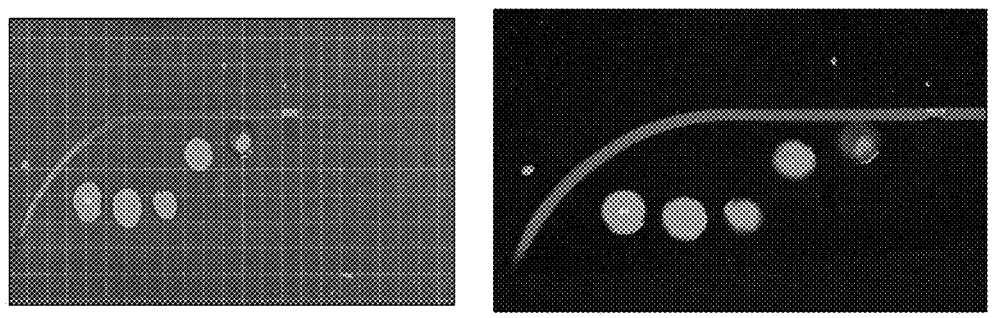
Figure 9B:
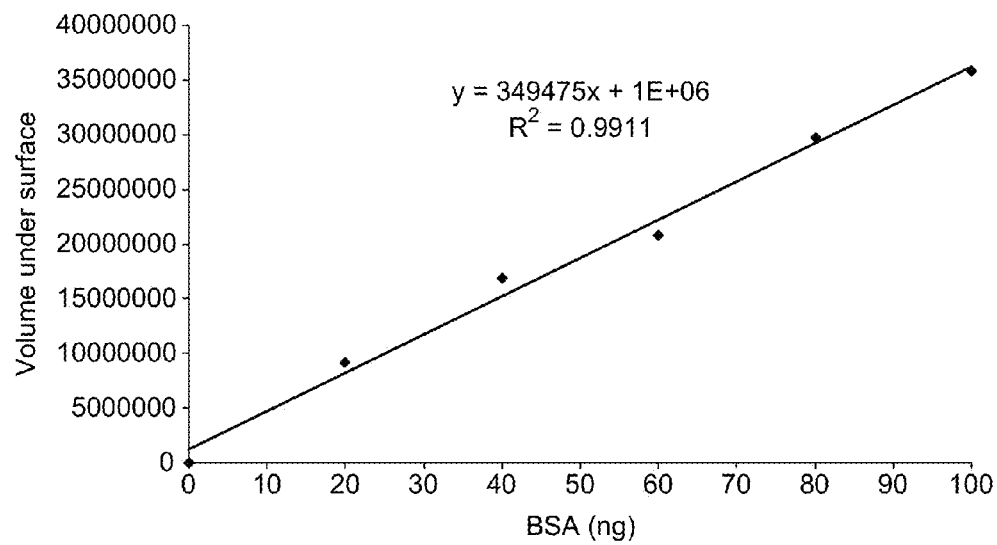

FIG. 9: shows the visualisation of protein matter and quantitation of BSA (0 to 100 nanograms) using the stabilised OPA/NAC reagent on a surgical blade. Image is captured using G-BOX and analysed using D-Plot software. The regression and linearity is calculated in Excel 2003.

Figure 10A:
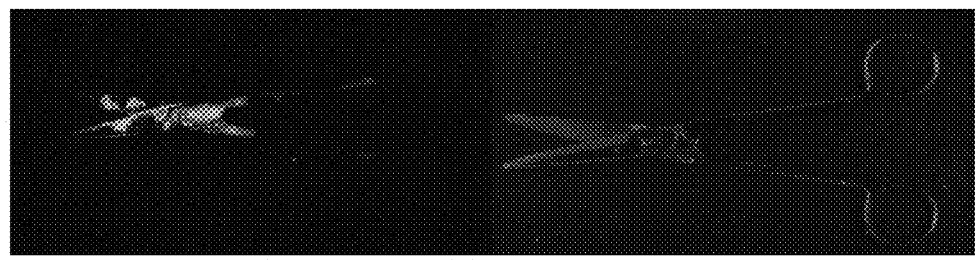
Figure 10B:
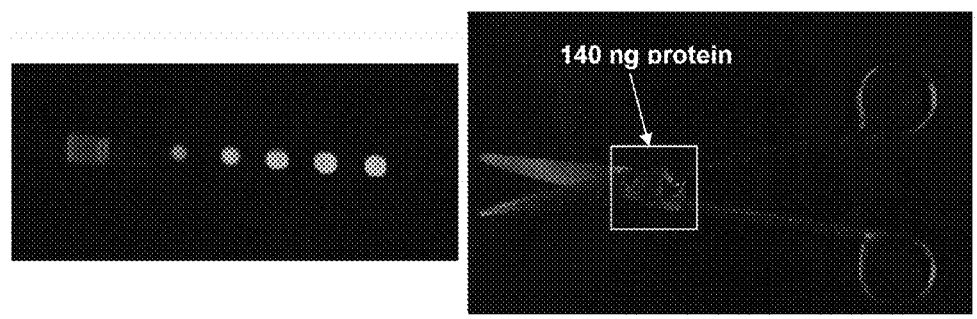

FIG. 10: shows the visualisation and quantification of protein residues on surgical instruments.

Figure 11A:
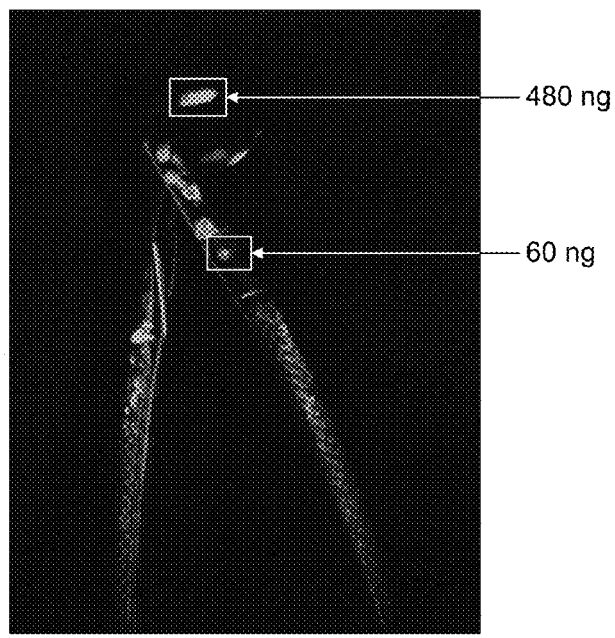
Figure 11B:
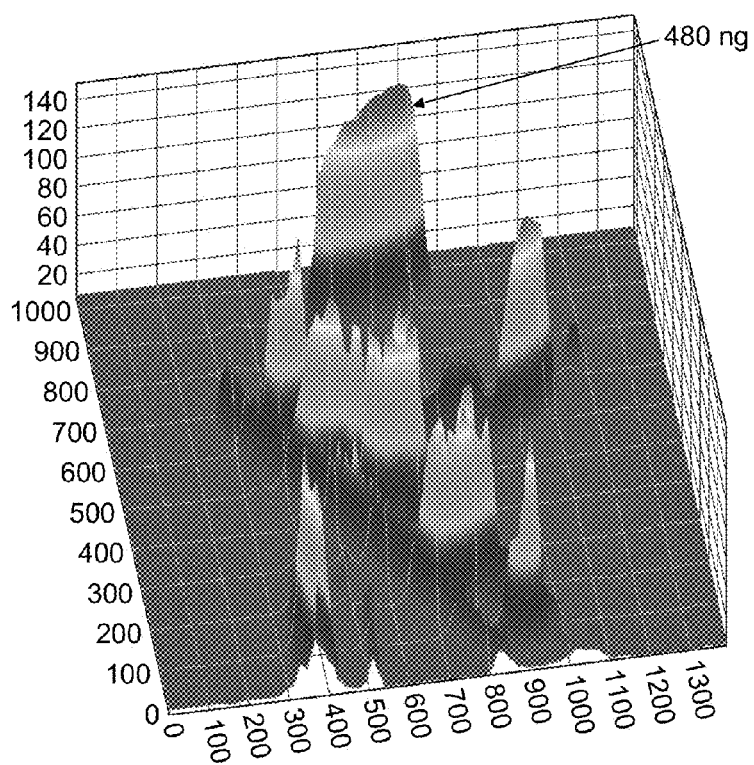
Figure 11C:
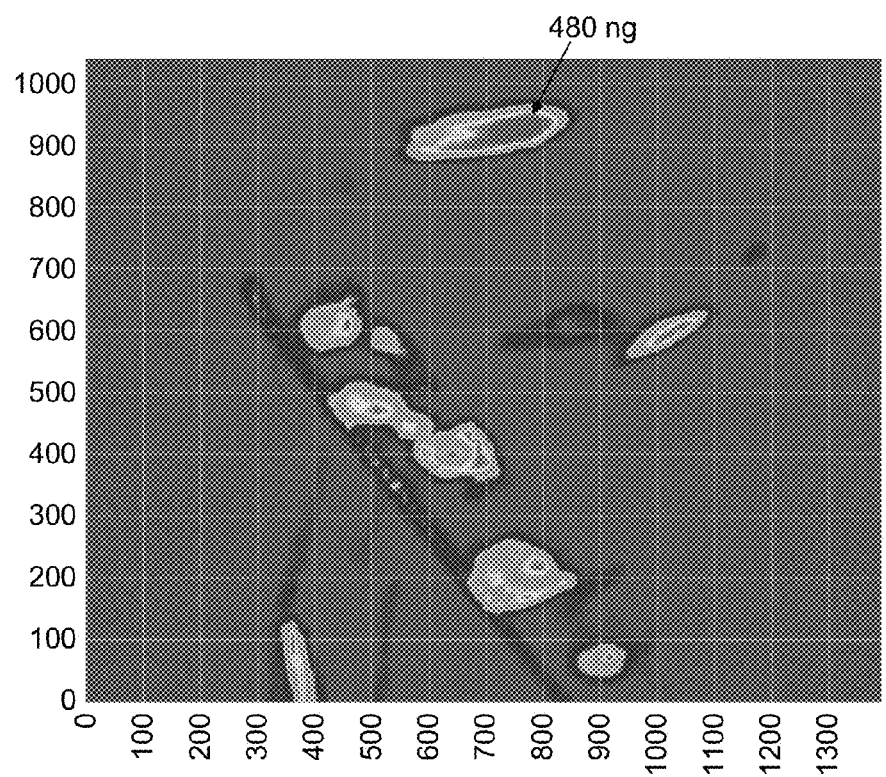

FIG. 11: shows the quantitative analysis obtained using the composition of the present invention on a set of stainless steel forceps; FIG. 10 (a) shows the screen shot of a false colour overlay of a set of forceps after SSD cleaning showing the residual protein present at different intensities on different sites of the forceps; FIG. 10 (b) shows a 3-D plot which is generated showing the varying quantities of residual protein present on the forceps; and FIG. 10 (c) shows the plot of protein intensities.

Figure 12A:
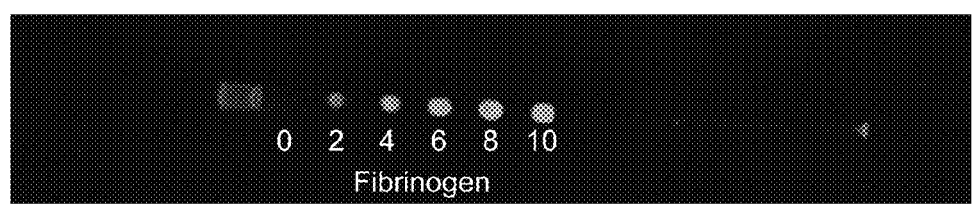
Figure 12B:
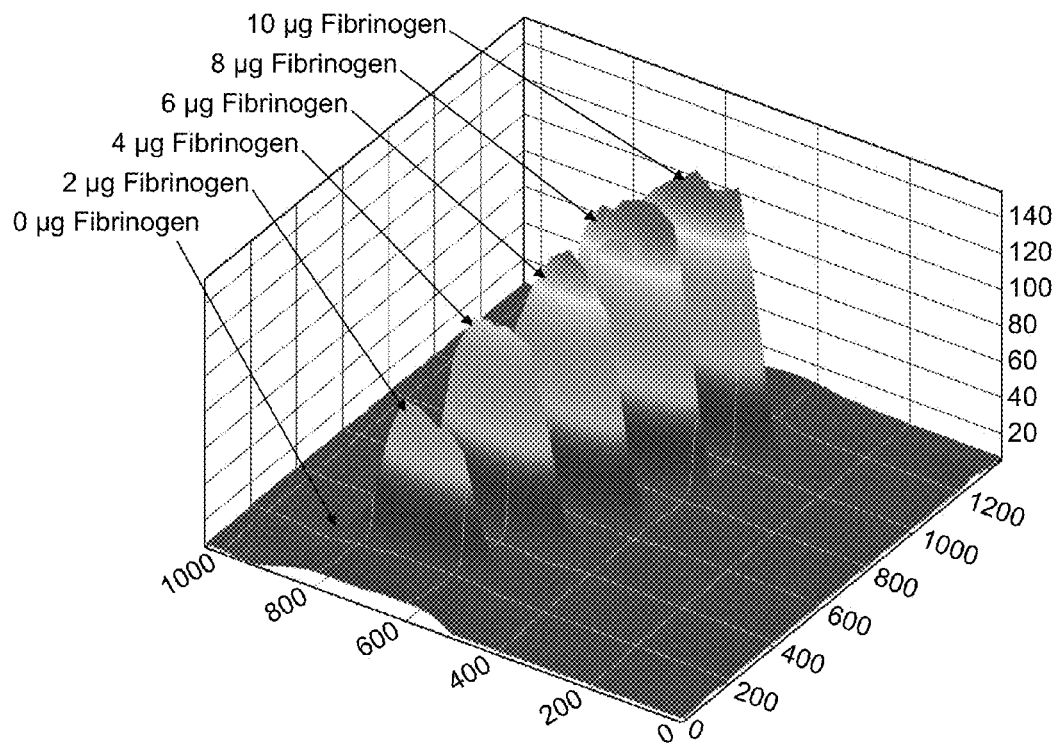
Figure 12C:
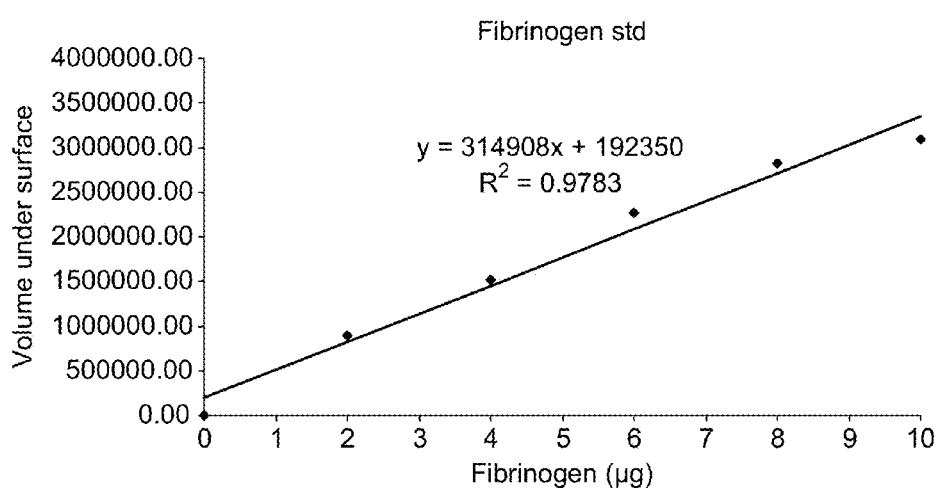

FIG. 12: shows the results from a Fibrinogen standard. FIG. 12 (a) shows the fluorescence emitted and captured in a false colour overlay screen shot of the varying standards of Fibrinogen; FIG. 12 (b) shows the 3 D plot which is generated showing the varying quantities of the standard; and FIG. 12(c) shows the standard curve for Fibrinogen.

EXAMPLES

Example 1

Preparation of OPA/NAC Reagent

Sodium borate buffer pH 9.23 was prepared by dissolving 9.5 g of Di-sodium tetraborate decahydrate in 500 ml of deionised H2O with several drops of 1 M NaOH to adjust the pH. Then 60 mg of N-Acetyl-L-Cysteine were added to the buffer solution and stirred with a magnetic stirrer until completely dissolved. The OPA solution was prepared by dissolving 60 mg of OPA in 5 ml of methanol and then this solution was added into the borate buffer solution. The OPA/NAC reagent solutions were prepared weekly and stored refrigerated in the dark at +4° C. for 24 h before use in order to reduce the background fluorescence.

Example 2

Preparation of the Stabilised OPA/NAC for Protein Detection

Sodium borate buffer pH 9.23 was prepared by dissolving 19 grams of Di-sodium tetraborate decahydrate in 900 ml of deionised $H_2O$ with several drops of 1 M NaOH to adjust the pH. Then 1 ml of Triton® X-100, 1.63 g of N-Acetyl-L-Cysteine, 0.077 g of DTT were added to the buffer solution and stirred with a magnetic stirrer until completely dissolved. The OPA solution was prepared by dissolving 0.268 g OPA in 10 ml methanol and then the OPA solution was added into the borate buffer solution. The solution was made up to 1 L. The OPA/NAC solution was stored refrigerated in the dark at +4° C. for 24 hours before use in order to reduce the background fluorescence.

Example 3

Preparation of the Stabilised OPA/NAC Reagent Further Comprising Sodium EDTA

The same OPA solution as described in Example 2 was prepared with the addition of 0.32 g of disodium EDTA were added to the buffer solution and stirred with a magnetic stirrer until completely dissolved.

Example 4

Determining the Stability of the Stabilised OPA/MAC Reagent

To evaluate the stability and sensitivity of the stabilised OPA/NAC reagent inter assays with BSA were performed over a period of 6 months.

A standard assay with Bovine Serum Albumin was prepared. The standard BSA solutions were prepared and diluted with deionised water and made up to concentration ranges of 0-100 µg ml$^{-1}$. Blank measurements and standard assays with BSA were performed with freshly prepared and stored stabilised OPA/NAC reagent solutions (as described in Examples 2 and 3) stored both at room temperature and in the refrigerator, at 4° C. for various periods of time.

Reaction assays using the stabilised OPA/NAC reagent (mentioned in Example 2 and 3) with BSA were prepared in 1 cm acrylic PMMA or silica cell fluorescent cuvettes, that is 300 µl of the BSA concentration mixed thoroughly with 200 µl of stabilised OPA/NAC reagent allowed the reaction mixture to stand for 5 minutes at room temperature before the fluorescence was measured at Excitation/Emission=350/450 nanometers.

The fluorescence emitted from the reaction from the isoindole products formed was measured with a HITACHI F4500 Fluorescence Spectrophotometer. The Spectrophotometer was set at excitation and emission 350 nanometers and 450 nanometers wavelengths respectively with band widths of 10 nanometers excitation and 2.5 nanometers emission and a PM voltage of 700 Volts. The data was then used to calculate the limit of detection of the reagent with respect to protein detection.

The reagent sensitivity was stable at room temperature for up to 3 months at room temperature. The results shown in FIG. 2 indicate that the reagent sensitivity was stable for up to 6 months at 4° C. The linearity of the BSA standards is 0.99 over the six months period and the sensitivity is 36±3.2 µg mL$^{-1}$/RFU (Table 1).

TABLE 1

Stability and sensitivity of stabilised OPA/NAC reagent with BSA over 6 month storage period.

| Time | Linearity | R$^2$ | L.o.D µg/mL @S/N = 2 |
| --- | --- | --- | --- |
| Day 2 | y = 39.9x + 77.1 | 0.99 | 1.9 |
| 1 month | y = 39.5x + 80.7 | 0.99 | 2.0 |
| 2 months | y = 37.8x + 112.2 | 0.99 | 2.9 |
| 3 months | y = 36.3x + 145.5 | 0.99 | 4.0 |
| 4 months | y = 34.9x + 172.7 | 0.99 | 4.9 |
| 5 months | y = 32.3x + 173.3 | 0.99 | 5.3 |
| 6 months | y = 32.0x + 66.09 | 0.99 | 2.1 |

Reaction rate of the stabilised OPA/NAC with proteins and the development of fluorescence is very rapid with a completion time of <3 minutes. In fact, in the imaging system fluorescence development was complete by the time the image was first captured.

Example 5

Determining the Stability of the Stabilised OPA/NAC Reagent Products Formed after Reaction with Protein Matter To evaluate the stability of the isoindole products formed, assays of 10 replicates of a known concentration were prepared and mixed with stabilised OPA/NAC reagent (as mentioned in Example 4) in a fluorescent cuvette. This was achieved by measuring the fluorescence from the isoindole products at time intervals to compare the products loss in fluorescence detection.

The fluorescence emitted from the reaction mixture was detected after allowing the reaction mixture to stand for 5 minutes (as mentioned in Example 4) at room temperature before measuring the fluorescence at Excitation/Emission=350/450 nanometers.

The reaction mixture was left for 360 minutes (6 hours) and the fluorescence from the reaction mixture measured at intervals of an hour to detect the stability of the isoindole products.

This example shows that not only the stabilised OPA/NA reagent is stable over 6 months but the isoindole products in solution are stable over a period of up to 6 hours.

Example 6

Specificity of the Stabilised OPA/NAC Reagent

Protein standard solutions (0 to 100 μg/ml) containing BSA, Haemoglobin, Fibrinogen, Cytochrome-C, Globulin, Myoglobin, were prepared in deionised water as mentioned in Example 2. The reproducibility of the method was evaluated by repeated analysis of BSA and cytochrome-C with 10 replicates of each.

The fluorescence measured with the spectrophotometer when using the stabilised OPA/NAC reagent with the different proteins gave a linear response with all the proteins tested (FIG. 4). The sensitivity varied with the nature of the protein. The limit of detection for BSA in the system was 0.3 μg/mL (Table 2)

TABLE 2

Sensitivity of stabilised OPA/NAC reagent with proteins in aqueous solution.

| Protein | Linearity | $R^2$ | Sensitivity (μg/mL/RFU) |
| --- | --- | --- | --- |
| Fibrinogen | y = 8.705x + 122.1 | 0.99 | 9 |
| Cyt-C | y = 19.69x + 203.2 | 0.97 | 20 |
| Globulin | y = 23.84x + 295.8 | 1.00 | 24 |
| BSA | y = 34.84x + 22.69 | 1.00 | 35 |
| Haemoglobin | y = 46.27x + 206.1 | 1.00 | 46 |
| Myoglobin | y = 49.23x + 292.9 | 0.99 | 49 |

Example 7

In Situ Detection of Protein Residues on Surgical Instruments

The stabilised OPA/NAC reagent (as described in Example 2 and 3) was used to detect protein residues in situ on surfaces. The advantage of detecting protein residues in situ means that all amino acid and ammonia residues have been removed by a simple water wash.

A standard assay with BSA was prepared (as mentioned in Example 4).

Protein visualisation experiments were carried out using a modified gel documentation system (G-BOX) from SYN-GENE (Cambridge, UK). The system using mercury lamps with phosphorescence tubes optimised to give a excitation wavelength of 350 nm very close the optimal for the OPA/NAC reagent. The emitted light was captured by a cooled CCD camera after passing through a 440 nm interference filter (i.d. 7 cm). Spray bottles were from a high street pharmacy. All spraying was done on sheets of black non-fluorescent art paper, which were changed after each use.

Semi-quantitative analysis of the G-BOX images was done using a software programme D-Plot from HydeSoft Computing, Vicksburg, USA.

Protein spots were pipetted on to stainless steel surfaces and allowed to air dry at room temperature for at least 4 hours before investigation. The instrument and/or surface was placed on the platform and sprayed with a fine mist of the stabilised OPA/NAC reagent. The chamber of the platform was closed and a series of subsequent images captured with first white light and then UV (350 nanometers) at exactly the same setting on the camera. The images are superimposed with a false colour and the protein spots are used for qualitative (FIG. 5) and semi quantitative analysis (please refer to Example 8).

Example 8

Semi Quantitative Analysis

The images captured were imported into the D-Plot software program. The images were converted from a bitmap to 3D using the software L plug-in. The plug-in maps pixel values of images to z values in a surface plot. The volume under the surface of the fluorescent spots is measured as a measure of the intensity of the fluorescence. The value is used for the quantitative analysis.

A: Stability of the Dry Fluorescent Derivatives.

The reagent is stable up to 6 months at 4° C. A 4 month old reagent was used in detecting protein on a surgical scalpel blade (FIG. 6). Surprisingly, the formed fluorophores fluoresced even after 9 months when left in open air. This is shown in FIG. 7.

B: Sensitivity of the Stabilised OPA/NAC Reagent in Detecting Protein Spots in Situ.

Standard protein (BSA) was used to determine the sensitivity of the system in detecting protein residues on instrument stainless steel surfaces. BSA (0 to 1200 ng) in 1 μl spots (2 mm$^2$) were pipetted on a clean stainless steel surface and dried at room temperature. The spots were then sprayed with the stabilised OPA/NAC reagent and analysed as described in Examples 5 and 6. The volume under surface was plotted against the concentration to assay the linearity of the reagent for in situ protein visualisation (FIG. 8). The regression $R^2$ of the standard calibration was 0.98. The limit of detection using the defined system, is currently 500 picograms of protein per spot or 250 pg/mm$^2$. (FIG. 9)

C: Semi Quantitative Analysis of Protein Residues in Surgical Instruments.

In order to test the applicability of the developed system in detecting protein residues after the surgical instruments have been through a wash a hydrophobic protein (Fibrinogen) was used on a pair of scissors. The instrument was sprayed with OPA/NAC/DTT after contamination and washed in a typical SSD. The washed instrument was photographed and re-sprayed and subsequently photographed at the same settings. The image was analysed to quantify the protein residues remaining.

Results show that any remaining protein can be visualised and quantified. In this particular case there was 140 ng of fibrinogen remaining as calculated from the calibration of fibrinogen (FIG. 9). In order to achieve this, the protein area was manually outlined with D-Plot. The volume of the fluorescence within the protein spot was calculated by D-plot and the actual amount of protein is calculated by reference to a series of standard spots as shown in FIG. 12. It is clear that with suitable edge detection software and a protein calibrant, this process could be automated and simplified. The regression and linearity is calculated in Excel 2003.

Discussion

Instability of the OPA/NAC solution/reagent is caused by the formation of disulphide bridges between thiols present in the reagent mixture; this does not allow OPA to combine with the thiol in the solution to form the reacting reagent hence its loss in sensitivity and stability over time. The stability of the solution/reagent was achieved by the addition of thiol-reducing compounds such as DTT (dithithreitol) or TCEP (Tris 2-carboxyethyl phosphine hydrochloride).

Stabilisation of Isoindoles Formed by Stabilised OPA/NAC Reagents

The secondary limitation of the OPA/NAC reagent is its production of unstable isoindole derivatives which lose the fluorescent signal rapidly in time. This causes time constraints when performing assays with this reagent.

Calculations and Statistics

Intra and inter assays of the reagents showed the reproducibility of the reactions and hence the validation of the reagents. Descriptive statistics (Mean, Standard deviation and Coefficient of variance) were calculated to show the significant improvement of the limit of detection of the stabilised OPA/NAC reagent. The limit of detection and quantification took into consideration 95% confidence intervals and were calculated with the following formula:

$$LoD=((CV \times 2)/100)) \times \text{mean concentration}$$

$$LoQ = LoD \times 2.5$$

Statistical calculations were performed using MS-Excel 2003.

The long term stability of the OPA/NAC reagent exhibited a loss in sensitivity from 76 µg ml$^{-1}$/RFU observed after 24 hours from its preparation down to 16 µg ml$^{-1}$/RFU 72 hours later. This confirmed the constant decay in the reagents stability.

The instability of the reagent originates from the thiol compound forming disulphide bridges within the reagent mixture rather than binding with OPA to react with the protein and/or amino acid to produce the isoindole derivatives of the reaction. In addition, the isoindole fluorophore derivatives are themselves unstable and give rise to loss of a signal after 30 minutes of the reaction taken place which causes a major limitation to the precision of any analytical study.

Introducing a thiol reducing compound into the reagent mixture has effectively reduced the formation of the disulphide bridges between the thiols in the reagent. The results show that it has even improved the long term stability of the reagent. In addition, the composition of this invention has shown to increase the sensitivity and stability of the reagent when reacted with BSA and the stability over time of the isoindole derivatives produced from the reaction mixture.

The stabilised OPA/NAC reagent enhances the long term stability of the reagent in comparison to the original and unstable OPA/NAC by maintaining a constant sensitivity signal over time.

The LoD's of the OPA/NAC reagents of the invention were calculated based upon the coefficient of variance from the intra assay variability performed. These confirmed that the addition of a thiol reducing agent and a chelating agent to the OPA/NAC reagent increased the limit of detection in reactions with BSA. The original OPA/NAC showed a LoD of ~840 ng ml$^{-1}$, the addition of DTT and EDTA at the required amounts to the OPA/NAC reagent showed a range of ~750-530 ng ml$^{-1}$ and the addition of TCEP showed a significant increase of LoD for the reagent which ranged from 700 down to 10 ng ml$^{-1}$.

Isoindole Stabilisation

The original OPA/NAC showed 33% decay in fluorescence signal of its isoindole products 30 minutes after the initial measurement. In contrast the addition of TCEP showed ~2-80% increase of isoindole fluorescence signal whereas DTT demonstrated a range of ~1-27% decrease. The time dependency significantly showed variability with the amount and type of thiol reducing agent which is introduced into the OPA/NAC reagent mixture.

These results show that long term stability of the OPA/NAC reagent can be achieved by the addition of a thiol reducing agent. The addition of thiol reducing compounds show a greater LoD, less signal fluorescence variability and a constant stability with age of the reagent and its products and with a detection limit at least 300 times more sensitive than ninhydrin in respect of protein detection.

The invention claimed is:

1. A protein and/or amino acid detecting composition comprising:
    (a) about 0.1 mmol/L to about 10 mmol/L or phthaldialdenyde,
    (b) about 1 mmol/L to about 20 mmol/L of a C3-C6 thiol selected from the group consisting of N-Acetyl-L-Cysteine (NAC), N-acetyl-D-peniciliamine, N-acetylcysteamine, N-acetyl-homocysteine, and mercaptosuccinic acid,
    (c) about 10 mmol/L to about 100 mmol/L of a buffer with a pH in the range of from about 7.5 to about 10, and
    (d) about 0.01% v/v to about 2% v/v of a surfactant, wherein the composition further comprises
    (e) about 0.05 mmol/L to about 5 mmol/L of a thiol reducing compound selected from Dithiothreitol, 2-mercaptoethylamine, and Tris (2-carboxyethyl) phosphine;
    wherein the composition is stable at 4° C. for 6 months and 3 months at room temperature.

2. The composition of claim 1, wherein the $C_3$-$C_6$ thiol is N-Acetyl-L-Cysteine.

3. The composition as claimed in claim 1, wherein the buffer has a pH in the range of pH 9 to pH 9.5.

4. The composition as claimed in claim 1, wherein the surfactant is a non-ionic surfactant.

5. The composition claimed in claim 1, further comprising a chelating agent.

6. The composition of claim 5, wherein the chelating agent is at a concentration of about 0.05 mmol/L to about 5 mmol/L.

7. The composition of claim 1, wherein the composition further comprises an organic solvent.

8. The composition of claim 7, wherein the solvent is selected from the group consisting of ethanol, methanol, acetone and acetonitrile.

9. The composition of claim 7, wherein the solvent is methanol.

10. A process for making the composition as claimed in claim 1, by mixing the components (a), (b), (d) and (e) into the buffer solution (c).

11. An in situ method for detecting protein and/or amino acid on a surface or substrate, comprising:
    a) applying the composition as claimed in claim 1 to a surface and/or substrate, and
    b) detecting fluorescence.

12. The method as claimed in claim 11, wherein the fluorescence is detected by any means or apparatus which is able to detect fluorescent light.

13. A kit for detecting protein and/or amino acid comprising:
    a) a composition as claimed in claim 1, and
    b) instructions for use.

14. A kit for detecting protein and/or amino acid in situ on a surface or substrate comprising:
   a) a composition as claimed in claim 1,
   b) means for applying the composition to a surface and/or substrate, and
   c) instructions for use.

* * * * *

UNITED STATES PATENT AND TRADEMARK OFFICE
CERTIFICATE OF CORRECTION

PATENT NO. : 9,541,557 B2  
APPLICATION NO. : 13/817540  
DATED : January 10, 2017  
INVENTOR(S) : David Perrett et al.

Page 1 of 1

It is certified that error appears in the above-identified patent and that said Letters Patent is hereby corrected as shown below:

In the Claims

In Claim 1, Line 7 should read:
-- Cysteine (NAC), N-acetyl-D-penicillamine, N-acetyl- --

Signed and Sealed this
Thirtieth Day of May, 2017

Michelle K. Lee
*Director of the United States Patent and Trademark Office*